(12) United States Patent
Kakuno et al.

(10) Patent No.: US 9,835,550 B2
(45) Date of Patent: Dec. 5, 2017

(54) BREATH ANALYZER

(71) Applicant: KABUSHIKI KAISHA TOSHIBA, Minato-ku (JP)

(72) Inventors: Tsutomu Kakuno, Fujisawa (JP); Shigeyuki Takagi, Fujisawa (JP); Yasutomo Shiomi, Koza (JP); Akira Maekawa, Kamakura (JP); Miyuki Kusaba, Meguro (JP); Hiroshi Hasegawa, Yokosuka (JP); Takashi Magara, Meguro (JP); Isao Muraoka, Tokorozawa (JP)

(73) Assignee: Kabushiki Kaisha Toshiba, Minato-ku (JP)

( * ) Notice: Subject to any disclaimer, the term of this patent is extended or adjusted under 35 U.S.C. 154(b) by 0 days.

(21) Appl. No.: 15/125,901

(22) PCT Filed: Sep. 24, 2015

(86) PCT No.: PCT/JP2015/076993
§ 371 (c)(1),
(2) Date: Sep. 13, 2016

(87) PCT Pub. No.: WO2016/147451
PCT Pub. Date: Sep. 22, 2016

(65) Prior Publication Data
US 2017/0227455 A1    Aug. 10, 2017

(30) Foreign Application Priority Data
Mar. 18, 2015 (JP) .................. 2015-054522

(51) Int. Cl.
*G01J 5/02* (2006.01)
*G01N 21/3504* (2014.01)
*G01N 33/497* (2006.01)

(52) U.S. Cl.
CPC ....... *G01N 21/3504* (2013.01); *G01N 33/497* (2013.01); *G01N 2033/4975* (2013.01); *G01N 2201/0612* (2013.01); *G01N 2201/12* (2013.01)

(58) Field of Classification Search
CPC .............. G01N 33/483; G01N 33/497; G01N 21/3504; G01N 2201/12; G01N 2033/4975; G01N 2201/0612; G06F 19/3431
See application file for complete search history.

(56) References Cited

U.S. PATENT DOCUMENTS 4,931,404 A    6/1990  Kundu
5,071,769 A  * 12/1991 Kundu .................. A61B 5/083
                                                     422/413

(Continued)

FOREIGN PATENT DOCUMENTS

JP    63-168565 A    7/1988
JP   2001-349888 A  12/2001

(Continued)

OTHER PUBLICATIONS

Kundu et al., "Breath Analyzer: Diagnostic Tool to Monitor Dietary Fat Loss," 1993, Clinical Chemistry, vol. 39, No. 1 pp. 87-92.*

(Continued)

*Primary Examiner* — Kiho Kim
(74) *Attorney, Agent, or Firm* — Oblon, McClelland, Maier & Neustadt, L.L.P.

(57) ABSTRACT

A breath analyzer includes a light source, a gas cell, a detection unit and a data processing unit. The light source emits infrared light of a wavelength band including an absorption line for acetone. A breath containing sample gas is introduced to the gas cell. The infrared light is incident on the gas cell. The detection unit receives transmitted light emerging from the gas cell, and outputs a sample signal (Continued)

value corresponding to an acetone discharge amount. The data processing unit determines an approximation formula of dependence of fat oxidation rate on acetone discharge amount in advance, and calculates a fat oxidation rate for individual sample signal values using the approximation formula. When the acetone discharge amount (microliter/min) is x, the fat oxidation rate (milligram/min) y is approximated by a following formula: $y=Ax+B$ (where A and B are constants).

15 Claims, 4 Drawing Sheets

(56) References Cited

U.S. PATENT DOCUMENTS

| | | | | |
|---|---|---|---|---|
| 6,454,723 | B1* | 9/2002 | Montagnino | A61B 5/083 |
| | | | | 600/531 |
| 8,088,333 | B2* | 1/2012 | Ahmad | A61B 5/083 |
| | | | | 422/50 |
| 8,722,417 | B2* | 5/2014 | Ahmad | A61B 5/097 |
| | | | | 422/400 |
| 8,932,525 | B1* | 1/2015 | Ahmad | G01N 33/497 |
| | | | | 422/50 |
| 2002/0007249 | A1* | 1/2002 | Cranley | A61B 5/00 |
| | | | | 702/24 |
| 2003/0208133 | A1* | 11/2003 | Mault | A61B 5/0002 |
| | | | | 600/532 |
| 2009/0056409 | A1* | 3/2009 | Howard | A61B 5/0836 |
| | | | | 73/1.07 |
| 2013/0288208 | A1* | 10/2013 | Yamada | G06F 19/3475 |
| | | | | 434/127 |
| 2014/0228698 | A1 | 8/2014 | Roeck et al. | |
| 2014/0377877 | A1* | 12/2014 | Burgi | G01N 33/4972 |
| | | | | 436/120 |
| 2015/0025811 | A1* | 1/2015 | Kodama | A61B 5/14546 |
| | | | | 702/19 |
| 2017/0016816 | A1 | 1/2017 | Takagi et al. | |
| 2017/0074857 | A1* | 3/2017 | Dennis | G01N 33/497 |

FOREIGN PATENT DOCUMENTS

| | | |
|---|---|---|
| JP | 4108297 B2 | 6/2008 |
| JP | 2009-188197 A | 8/2009 |
| JP | 2009-206340 A | 9/2009 |
| JP | 2014-21101 A | 2/2014 |
| JP | 2015-21744 A | 2/2015 |
| JP | 2015-40770 A | 3/2015 |
| JP | 2015-155803 A | 8/2015 |
| WO | WO 2015/019650 A1 | 2/2015 |
| WO | WO 2015/125323 A1 | 8/2015 |
| WO | WO 2015/125324 A1 | 8/2015 |
| WO | WO 2015/125327 A1 | 8/2015 |
| WO | WO 2015/125328 A1 | 8/2015 |
| WO | WO 2015-132986 A1 | 9/2015 |
| WO | WO 2015/136744 A1 | 9/2015 |

OTHER PUBLICATIONS

Deng et al., "Determination of acetone in human breath by gas chromatography-mass spectrometry and solid-phase microextraction with on-fiber derivatization," 2004, Journal of Chromatography, vol. B, No. 810, pp. 269-275.*

International Search Report and Written Opinion dated Dec. 1, 2015 in PCT/JP2015/076993 (with English language translation of Search Report only).

* cited by examiner

BREATH ANALYZER

TECHNICAL FIELD

This invention relates to a breath analyzer.

BACKGROUND ART

Health conditions can be found through analysis of the composition or the concentration of gases contained in the breath.

For example, the acetone produced in the conversion of the accumulated free fatty acids in the body into blood glucose discharges out of the body with the breath. If the body fat combustion rate could be estimated from the concentration or the discharge amount of acetone, it would be possible to use the information for health management such as dieting.

The detection accuracy of a semiconductor gas sensor is not sufficient for the measurement of the concentration or the discharge amount of trace amounts of acetone in the breath, and a gas chromatography mass spectrometer is too large for this purpose.

PRIOR ART DOCUMENT

Patent Document

[Patent Document 1] JP 2001-349888 A (Kokai)

SUMMARY OF INVENTION

Problem to be Solved by Invention

An object of the invention is to provide a breath analyzer that is small and has high detection accuracy, and is capable of calculating a fat oxidation rate.

Means for Solving Problem

A breath analyzer of an embodiment includes a light source, a gas cell, a detection unit and a data processing unit. The light source emits infrared light of a wavelength band including an absorption line for acetone. A breath containing sample gas is introduced to the gas cell. And the infrared light is incident on the gas cell. The detection unit receives transmitted light emerging from the gas cell, and outputs a sample signal value corresponding to an acetone discharge amount. The data processing unit, on the basis of the sample signal value, determines an approximation formula of dependence of fat oxidation rate on acetone discharge amount in advance, and calculates a fat oxidation rate for individual sample signal values using the approximation formula. When the acetone discharge amount (microliter/min) is x, the fat oxidation rate (milligram/min) y is approximated by a following formula: y=Ax+B (where A and B are constants).

EMBODIMENTS OF INVENTION

An embodiment of the invention is described below with reference to the accompanying drawings.

Figure 1:
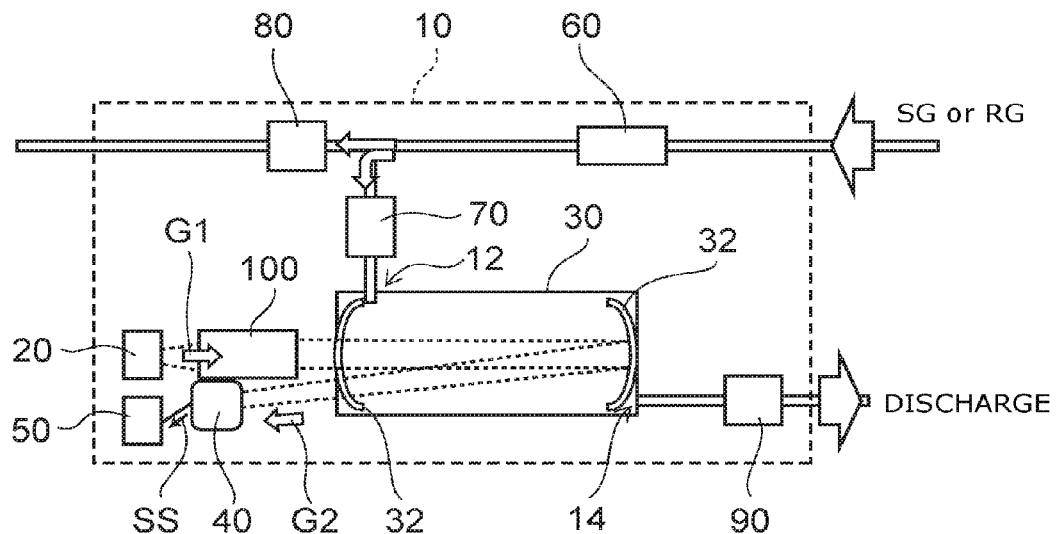
FIG. 1 is a diagram representing a configuration of the breath analyzer according to the embodiment.

FIG. 1 is a diagram representing a configuration of the breath analyzer according to the embodiment.

A breath analyzer 10 includes a light source 20, a gas cell 30, a detection unit 40, and a data processing unit 50.

The light source 20 emits infrared light G1 of a wavelength band that includes at least one absorption line for acetone. The light source 20 may be configured from light-emitting devices such as a QCL (Quantum Cascade Laser), and a semiconductor laser.

The gas cell 30 has an inlet 12 and an outlet 14. A sample gas SG such as breath, or a reference gas (for example, the atmosphere) RG is introduced into the gas cell 30. Infrared light G1 is incident on the gas cell 30. Displacement of the gas inside the gas cell 30 can be accelerated by providing a vacuum pump 90 at the outlet 14 of the gas cell 30.

The detection unit 40 receives transmitted light G2 emerging from the gas cell 30, and outputs a sample signal value SS corresponding to the acetone discharge amount or the acetone concentration.

The data processing unit 50 determines an approximation formula of dependence of fat oxidation rate on acetone discharge amount in advance, and calculates a fat oxidation rate corresponding to the sample signal value SS of each measured acetone discharge amount. Alternatively, the data processing unit 50 determines an approximation formula of dependence of fat oxidation rate on acetone concentration, and calculates a fat oxidation rate corresponding to the sample signal value SS of each measured acetone concentration. When an approximation formula obtained by using a measurement system (FIG. 4; described later) is input to the data processing unit 50 in advance, it is possible to accelerate the online calculation of the fat oxidation rate for individual sample signal values SS.

The acetone concentration calculation method is described below.

Absorbance A is represented by the Lambert-Beer law (Formula (1)). Absorption coefficient $\alpha$ is determined by the intensity of the absorption line, the pressure, and the temperature.

$$A = -\ln\left(\frac{I}{I_0}\right) = -\ln T = \alpha L \tag{1}$$

where
A: Absorbance
$I_0$: Intensity of incident light
I: Intensity of transmitted light
$T=I/I_0$: Transmittance
$\alpha$: Absorption coefficient
L: Light path length When a reference gas RG such as the atmosphere is introduced into the gas cell 30, the intensity I of the light that has passed through the reference gas RG can be regarded as the same as the incident light intensity $I_0$. On the other hand, by displacing inside of the gas cell 30 with a sample gas SG, transmittance T or absorbance A can be calculated from formula (1) by measuring the intensity I of the transmitted light through the sample gas SG.

The absorbance is represented by the following formula.

Absorbance=$1-I/I_0=1-T$

The absorption coefficient $\alpha$ can be represented by formula (2). Here, the absorption coefficient $\alpha$ is dependent on the intensity, the pressure, and the temperature.

$$\alpha = \in c \quad (2)$$

where c: Molar concentration $\alpha$: Molar absorption coefficient

Following formulae (1) and (2), the molar concentration c of acetone can be given by formula (3).

$$c = -\left(\frac{1}{\varepsilon L}\right) \times \ln T \quad (3)$$

The gas flow control system is described below. The flow rates of the breath sample gas SG and the reference gas RG are measured with a flowmeter 60, and the total discharge amount can be found by integrating the flow rate through the flowmeter 60. The sample gas SG and the reference gas RG that have passed through the flowmeter 60 are branched. The flow rate of the gas flow directed toward the gas cell 30 is controlled at a constant rate with a flow rate restriction mechanism 70. The flow rate control mechanism 70 may be, for example, a mass flow controller, or a needle valve. The gas that has passed through the flow rate restriction mechanism 70 is introduced into the gas cell 30 through the inlet 12. The other gas flow discharges out of the system through a needle valve 80. The system components, including the flowmeter 60, the flow rate restriction mechanism 70, and the vacuum pump 90 may be automated under the control of a controller (not illustrated).

The absorption spectrum of acetone has a plurality of absorption lines. In the embodiment, the infrared wavelength is, for example, 8.125 μm (corresponding to a wavenumber of 1,230.8 cm$^{-1}$). The influence of absorption by water can be reduced with this wavelength. Preferably, the wavelength of the infrared light G1 from the light source 20 is accurately tuned to at least one absorption line. For example, when using a QCL, current modulation may be performed to provide a wavelength range that includes a predetermined absorption line. This enables accurately measuring transmittance T at the absorption line wavelength, and determining the absorption coefficient $\alpha$, and the molar concentration of acetone.

Figure 2:
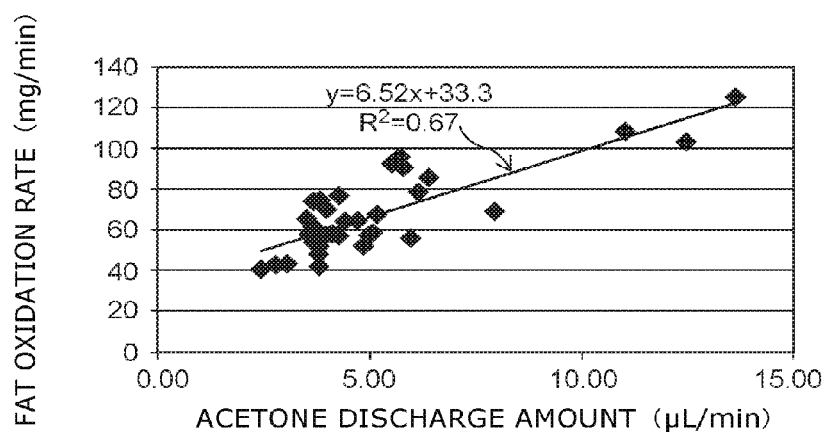
FIG. 2 is a graph showing the dependence of fat oxidation rate on the total acetone discharge amount.

FIG. 2 is a graph showing the dependence of fat oxidation rate on the total acetone discharge amount.

The vertical axis represents fat oxidation rate (mg/min) Y, and the horizontal axis represents the total acetone discharge amount (μl/min) X. FIG. 2 shows the dependence of fat oxidation rate at rest. However, the graph may be of during activity. The fat oxidation (combustion) rate can be measured using an automatic metabolism measurement device. For example, the fat oxidation rate may be determined by measuring parameters such as an oxygen intake amount, and a carbon dioxide discharge amount.

The acetone discharge amount x is determined as the product of breath discharge amount and acetone concentration. The breath discharge amount may be measured with the flowmeter 60.

From a distribution of measurement points, the fat oxidation rate y and the acetone discharge amount x have a correlation. The correlation is given as a linear function using the method of least squares, as represented by the following formula (4).

$$y = Ax + B \quad (4)$$

where A and B are constants.

Referring to FIG. 2, the linear function may be, for example, y=6.52x+33.3. In this case, the determination coefficient $R^2$ was 0.68 as measured by subtracting the residual sum of squares and the sum of squares of the differences from the sample average from 1. The dependence of fat oxidation rate on acetone concentration during activity also may be approximated by a linear function or the like. Considering parameters such as sex differences and age, the coefficient A and the coefficient B may be determined within appropriate ranges, specifically, 6 or more and 7 or less for coefficient A, and 0 or more and 50 or less for coefficient B.

Figure 3:
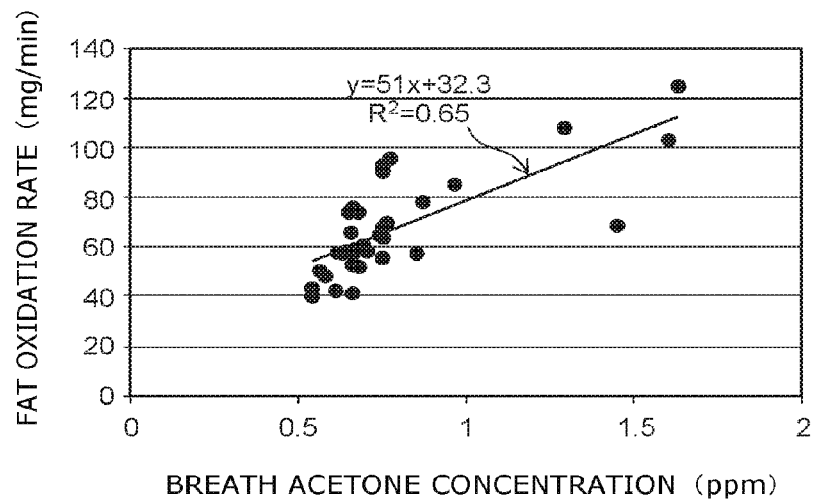
FIG. 3 shows the dependence of fat oxidation rate at rest. However, the graph may be of during activity.

FIG. 3 is a graph showing the dependence of fat oxidation rate on the breath acetone concentration.

The vertical axis represents fat oxidation rate (mg/min) y, and the horizontal axis represents the breath acetone concentration (ppm) x.

FIG. 3 shows the dependence of fat oxidation rate at rest. However, the graph may be of during activity.

From a distribution of measurement points, the fat oxidation rate y and the breath acetone concentration x have a correlation. The correlation is given as a linear function using the method of least squares, as approximated by the following formula (5).

$$y = Cx + D \quad (5)$$

where C and D are constants.

The linear function may be, for example, y=51x+32.3. In this case, the determination coefficient $R^2$ was 0.65. Considering parameters such as sex differences and age, the coefficient C and the coefficient D may be determined within appropriate ranges, specifically, 40 or more and 60 or less for coefficient C, and 0 or more and 50 or less for coefficient D.

The fat oxidation rate can be estimated by measuring the acetone concentration (ppm) and the acetone discharge amount in the breath sample gas SG of interest with the breath analyzer 10 shown in FIG. 1. For example, it is possible to promote health by making dieting plans based on the fat oxidation rate and the body weight, taking into account circumstances such as diet, and exercise.

The absorption efficiency can be improved by introducing the infrared light G1 from the light source 20 into the gas cell 30 after condensing the infrared light G1 with an optical system 100. It is also preferable to increase the light path length L by providing, for example, a reflecting mirror 32 inside the gas cell 30 because it can increase the absorbance A of acetone, which has a small absorption coefficient $\alpha$.

As shown in FIGS. 2 and 3, calculations of fat oxidation rate from individual sample signal values SS such as an acetone concentration and an acetone discharge amount become easier when the relation between fat oxidation rate and acetone concentration or acetone discharge amount is expressed beforehand as an approximation formula.

As a comparative example, a semiconductor gas sensor for acetone detection is available that includes, for example, a porous film containing at least one oxide, for example, tin oxide or indium oxide, one or more oxides of, for example, tungsten and molybdenum, and an element such as platinum. However, such a semiconductor gas sensor is insufficient in terms of selectivity and sensitivity. On the other hand, a gas chromatography analyzer requires highly skilled knowledge, in addition to being large and expensive. Such devices are accordingly difficult to use in homes. The device of the embodiment, on the other hand, has high sensitivity and high accuracy, and is small enough for use by ordinary users.

Figure 4:
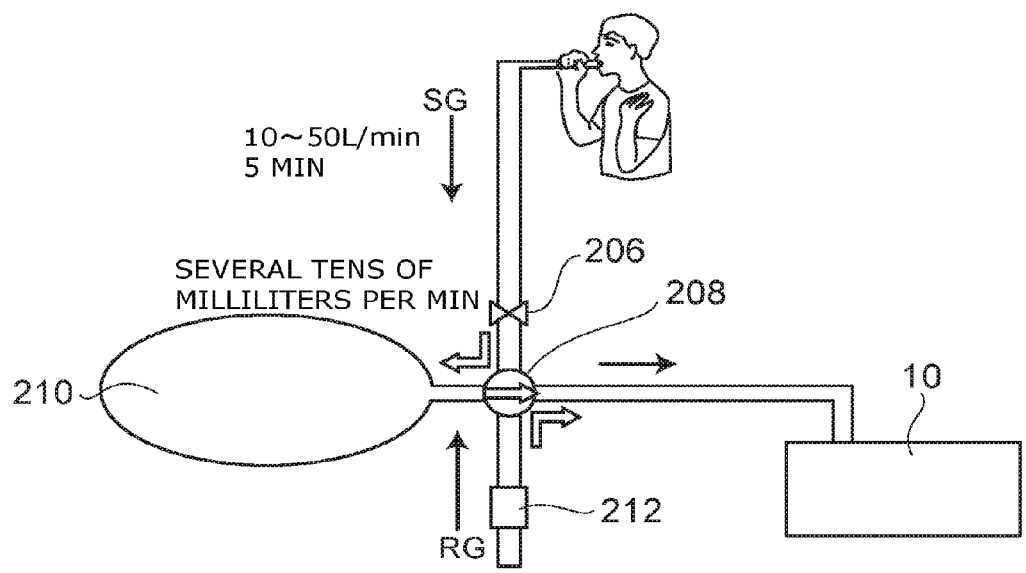
FIG. 4 is a diagram representing a configuration of a measurement system that calculates the acetone concentration or the acetone discharge amount offline.

FIG. 4 is a diagram representing a configuration of a measurement system that calculates the acetone concentration or the acetone discharge amount offline.

The measurement system includes the breath analyzer 10 of the embodiment, an on-off valve 206, a switch valve 208, and a Douglas bag 210, among other components.

The fat oxidation rate (or the body fat combustion rate) can be calculated by measuring, for example, an oxygen intake amount, and a carbon dioxide discharge amount with the metabolism measurement device.

The breathing rate of human is, for example, 10 to 50 liters/min. For offline measurement, for example, the breath is collected in a sampling bag 210 for a total of 30 minutes (10 min×3 times), using the on-off valve 206, and the switch valve 208. The sample gas SG that has accumulated in the sampling bag 210 is then sent to the breath analyzer 10 by switching the switch valve 208. The reference gas RG, for example, the atmospheric gas, is sent to the breath analyzer 10 after being cleaned with a chemical substance removing filter 212.

Figure 5A:
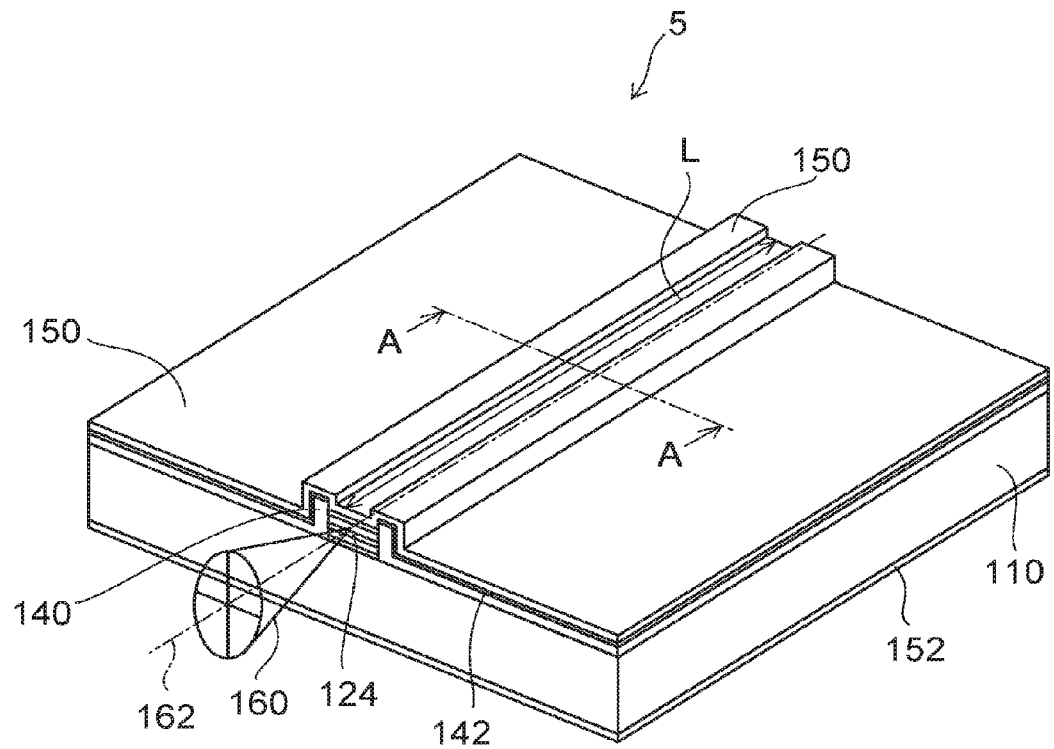
FIG. 5A is a schematic perspective view of a cutaway portion of a QCL.
Figure 5B:
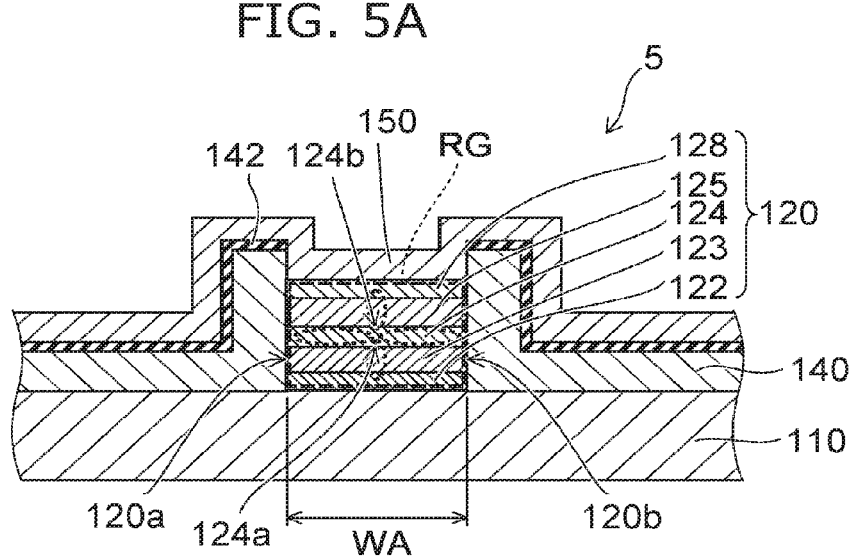
FIG. 5B is a schematic cross sectional view taken at line A-A.

FIG. 5A is a schematic perspective view of a cutaway portion of a QCL. FIG. 5B is a schematic cross sectional view taken at line A-A.

A QCL 5 includes at least a substrate 110, a stacked body 120 provided on the substrate 110, and a dielectric layer 140. Referring to FIG. 5A, the QCL also includes a first electrode 150, a second electrode 152, and an insulating film 142.

The stacked body 120 has a first cladding layer 122, a first guide layer 123, an active layer 124, a second guide layer 125, and a second cladding layer q28. The refractive indices of the first cladding layer 122 and the second cladding layer 128 are smaller than the refractive index of any of the first guide layer 123, the active layer 124, and the second guide layer 125 so that an infrared laser beam 160 can be properly trapped in the stacked direction of the active layer 124.

The stacked body 120 has a stripe shape, and can be called ridge waveguide RG. Assuming that the two end faces of the ridge waveguide RG are mirror surfaces, the light of stimulated emission is emitted as an infrared laser beam 162 through the light-emitting surface. In this case, the optical axis 162 is defined as the line that connects the centers of the cross sections of the optical resonator with the mirror surface serving as a resonating surface. In other words, the optical axis 162 lies in the direction of extension of the ridge waveguide RG.

When the width WA in a direction parallel to a first surface 124a and a second surface 124b of the active layer 124 is too wide in a cross section perpendicular to the optical axis 162, a higher-order mode occurs in the horizontal traverse direction, and it becomes difficult to achieve high output. It becomes easier to control the horizontal traverse direction mode when the width WA of the active layer 124 is, for example, 5 to 20 μm.

By making the refractive index of the dielectric layer 140 smaller than the refractive index of any of the constituent layers of the active layer 124, the ridge waveguide RG can be configured along the optical axis 162 with the dielectric layer 140 provided on the both sides of side surfaces 120a and 120b of the stacked body 120.

Figure 6:
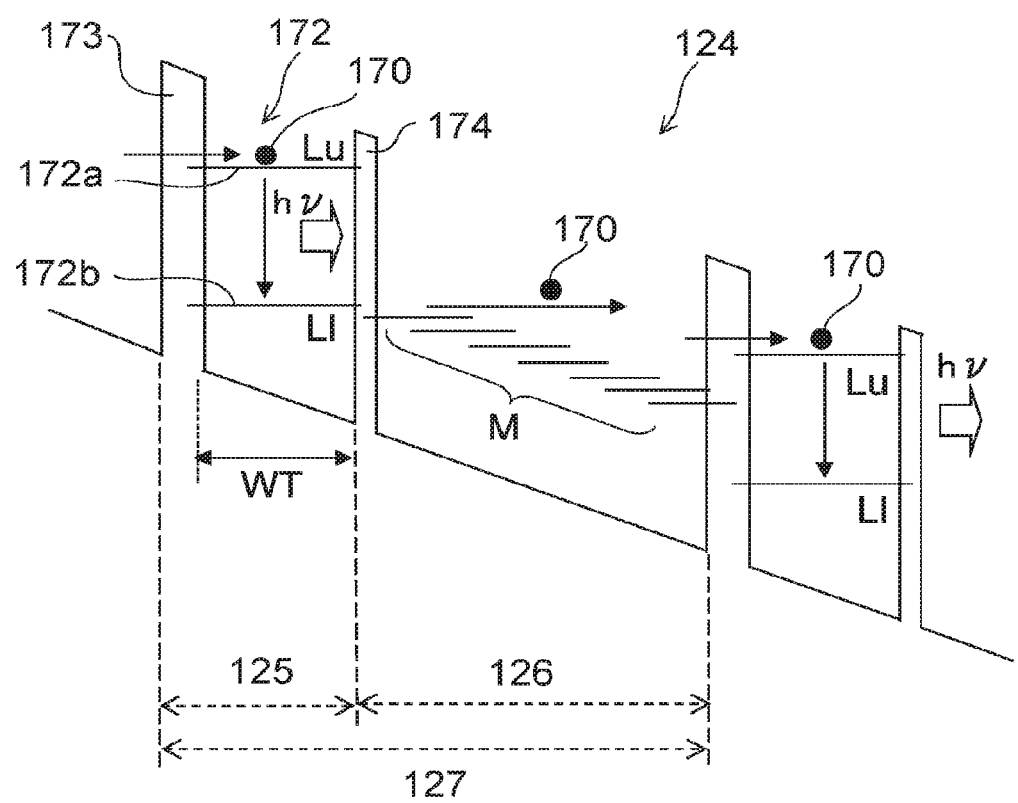
FIG. 6 is a band diagram describing the operation of the QCL.

FIG. 6 is a band diagram describing the operation of the QCL.

The active layer 124 has a cascade structure in which a first region 125 and a second region 126 are alternately stacked. Through an intersubband optical transition in a quantum well layer 172, the first region 125 can emit an infrared laser beam 60 that includes an absorption line of acetone. The second region 126 can relax the energy of electrons 170 injected from the first region 125.

Reducing the well width WT to, for example, several nanometers or less in the quantum well layer 172 causes the energy level to become discrete, and creates a subband 172a (high level Lu) and a subband 172b (low level Ll), for example. The injected electrons 170 from an injection barrier layer 173 become effectively trapped in the quantum well layer 72. When a carrier transition occurs from the high level Lu to the low level Ll, emission of light (hν) corresponding to the energy difference (Lu-Ll) occurs (optical transition). The quantum well layer 172 has a plurality of wells with overlapping wave functions, and may include common levels Lu and Ll.

An intersubband transition occurs in either the conduction band or the valence band. Specifically, a hole and electron recombination by p-n junction is not necessary, and emission occurs solely by the optical transition of either carrier. In the example represented in the figure, an intersubband transition occurs as the stacked body 120 injects the electrons 170 to the quantum well layer 172 via the injection barrier layer 173 under the applied voltage across the first electrode 150 and the second electrode 152.

The second region 126 has a plurality of subbands (or minibands as they are also called). Preferably, the subbands have small energy differences, and are a near continuous energy band. Because the electron energy is relaxed, an infrared laser beam including an absorption line for acetone does not occur in the second region 126. The low-level Ll electrons of the first region 125 are injected into the second region 126 through the extraction barrier layer 74, relaxed, and injected into the first region 125 on the next stage of the cascade connection (electrons 70) to cause the next optical transition. Specifically, the emission of an infrared laser beam by the optical transition is tuned within a spectrum range that includes an absorption line for acetone, for example, by varying the current.

In the QCL of the embodiment, the substrate 110 may be InP, the quantum well layer 172 may be InGaAs, and the barrier layer may be AlInAs, for example. In this case, the crystallinity of the active layer as a whole can improve when the quantum well layer and the barrier layer are strain compensated. The substrate 110 may be GaAs, the quantum well layer may be GaAs, and the barrier layer may be InGaAs, for example. The active layer 24 may have a width WA of 14 μm, and the ridge waveguide RG may have a length L of 3 mm, for example.

The embodiment provides a breath analyzer that is small and has high detection accuracy, and is capable of calculating a fat oxidation rate. The breath analyzer is useful for promoting health, and for dieting, for example.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

The invention claimed is:

1. A breath analyzer comprising:
   a light source that emits infrared light of a wavelength band including an absorption line for acetone;
   a gas cell to which a breath-containing sample gas is introduced, and on which the infrared light is incident;
   a detection unit that receives transmitted light emerging from the gas cell, and outputs a sample signal value corresponding to an acetone discharge amount; and
   a data processing unit that, on the basis of the sample signal value, determines an approximation formula of dependence of fat oxidation rate on acetone discharge amount in advance, and calculates a fat oxidation rate for individual sample signal values using the approximation formula,
   the fat oxidation rate (milligram/min) y being approximated by a following formula:

$$y=Ax+B,$$

where x is the acetone discharge amount (microliter/min), A is 6 or more and 7 or less, and B is 0 or more and 50 or less.

2. The analyzer according to claim 1, wherein A is 6.52, and B is 33.3.

3. The analyzer according to claim 1, wherein the acetone discharge amount is the product of a breath discharge amount and an acetone concentration.

4. The analyzer according to claim 3, further comprising a flowmeter for measuring the breath discharge amount.

5. The analyzer according to claim 3, wherein A is 6.52, and B is 33.3.

6. The analyzer according to claim 1, wherein the light source includes a quantum cascade laser.

7. The analyzer according to claim 6, wherein the quantum cascade laser has an InP substrate, and an active layer provided on the InP substrate, and including a quantum well layer containing InGaAs, and a barrier layer containing AlInAs.

8. The analyzer according to claim 7, wherein the quantum well layer and the barrier layer are strain compensated.

9. The analyzer according to claim 6, wherein the quantum cascade laser has a GaAs substrate, and an active layer provided on the GaAs substrate, and including a quantum well layer containing GaAs, and a barrier layer containing InGaAs.

10. A breath analyzer comprising:
    a light source that emits infrared light of a wavelength band including an absorption line for acetone;
    a gas cell to which a breath-containing sample gas is introduced, and on which the infrared light is incident;
    a detection unit that receives transmitted light emerging from the gas cell, and outputs a sample signal value corresponding to an acetone concentration; and
    a data processing unit that, on the basis of the sample signal value, determines an approximation formula of dependence of fat oxidation rate on acetone concentration in advance, and calculates an acetone concentration for individual sample signal values using the approximation formula,
    the fat oxidation rate (milligram/min) y being approximated by a following formula:

$$y=Cx+D,$$

where x is the acetone concentration (ppm), C is 40 or more and 60 or less, and D is 0 or more and 50 or less.

11. The analyzer according to claim 10, wherein C is 51, and D is 32.3.

12. The analyzer according to claim 10, wherein the light source includes a quantum cascade laser.

13. The analyzer according to claim 12, wherein the quantum cascade laser has an InP substrate, and an active layer provided on the InP substrate, and including a quantum well layer containing InGaAs, and a barrier layer containing AlInAs.

14. The analyzer according to claim 13, wherein the quantum well layer and the barrier layer are strain compensated.

15. The analyzer according to claim 12, wherein the quantum cascade laser has a GaAs substrate, and an active layer provided on the GaAs substrate, and including a quantum well layer containing GaAs, and a barrier layer containing InGaAs.

* * * * *